United States Patent
Garza et al.

(10) Patent No.: US 9,663,666 B2
(45) Date of Patent: May 30, 2017

(54) USE OF HYDROXYACID TO REDUCE THE LOCALIZED CORROSION POTENTIAL OF LOW DOSE HYDRATE INHIBITORS

(71) Applicant: Baker Hughes Incorporated, Houston, TX (US)

(72) Inventors: Timothy Z. Garza, Dickinson, TX (US); Stuart Edward Cook, Houston, TX (US); Gordon T. Rivers, Houston, TX (US); Vu Thieu, Houston, TX (US); Paul Robert Stead, Sugar Land, TX (US)

(73) Assignee: BAKER HUGHES INCORPORATED, Houston, TX (US)

( * ) Notice: Subject to any disclaimer, the term of this patent is extended or adjusted under 35 U.S.C. 154(b) by 199 days.

(21) Appl. No.: 14/602,943

(22) Filed: Jan. 22, 2015

(65) Prior Publication Data
US 2016/0215149 A1    Jul. 28, 2016

(51) Int. Cl.
  *C09D 5/08*   (2006.01)
  *C07C 7/20*   (2006.01)
  *C07C 63/06*  (2006.01)
  *C07C 9/04*   (2006.01)

(52) U.S. Cl.
  CPC .............. *C09D 5/084* (2013.01); *C07C 7/20* (2013.01); *C07C 9/04* (2013.01); *C07C 63/06* (2013.01)

(58) Field of Classification Search
  None
  See application file for complete search history.

(56) References Cited

U.S. PATENT DOCUMENTS

| | | |
|---|---|---|
| 2,758,970 A | 8/1956 | Saukaitis et al. |
| 2,814,593 A | 11/1957 | Beiswanger et al. |
| 2,993,863 A | 7/1961 | Monroe et al. |
| 3,077,454 A | 2/1963 | Monroe et al. |
| 3,107,221 A | 10/1963 | Harrison et al. |
| 3,382,179 A | 5/1968 | Keeney et al. |
| 3,404,094 A | 10/1968 | Keeney |
| 3,514,410 A | 5/1970 | Engle et al. |
| 3,773,465 A | 11/1973 | Keeney et al. |

(Continued)

FOREIGN PATENT DOCUMENTS

WO    2007030435 A1    3/2007

OTHER PUBLICATIONS

I. Sekine, et al., "Analysis for Corrosion Behavior of Mild Steels in Various Hydroxy Acid Solutions by New Methods of Surface Analysis and Electro-Chemical Measurements," J. Electrochemical Soc., vol. 137, No. 10, Oct. 1990, pp. 3029-3033.

(Continued)

*Primary Examiner* — Joseph D Anthony
(74) *Attorney, Agent, or Firm* — Mossman Kumar & Tyler PC

(57) ABSTRACT

Corrosion of metal conduits by hydrate inhibitor formulations, particularly localized corrosion, is mitigated when the hydrate inhibitor formulation contains an effective amount of at least one hydroxyacid or equivalent selected from the group consisting of hydroxyacids having 2 to 20 carbon atoms and at least one hydroxyl group. The hydrate inhibitor formulation has an absence of methanol, but may include other alcohol solvents, diol or triol solvents, aromatic solvents and ketone solvents.

17 Claims, 1 Drawing Sheet

(56) References Cited

U.S. PATENT DOCUMENTS

| | | | |
|---|---|---|---|
| 3,992,313 A | 11/1976 | Anderson et al. | |
| 4,104,303 A | 8/1978 | Anderson et al. | |
| 4,246,030 A | 1/1981 | Lipinski | |
| 4,871,024 A | 10/1989 | Cizek | |
| 4,997,040 A | 3/1991 | Cizek | |
| 5,366,643 A | 11/1994 | Walker | |
| 5,591,381 A | 1/1997 | Walker | |
| 6,251,836 B1* | 6/2001 | Duncum | C09K 8/52 507/123 |
| 6,596,911 B2 | 7/2003 | Przybylinski et al. | |
| 7,264,653 B2 | 9/2007 | Panchalingam et al. | |
| 7,417,010 B2* | 8/2008 | Collins | C09K 8/52 166/305.1 |
| 8,575,358 B2* | 11/2013 | Rivers | C07C 7/20 548/215 |
| 8,618,025 B2 | 12/2013 | Webber | |
| 2005/0170974 A1* | 8/2005 | Collins | C09K 8/52 507/219 |
| 2005/0261529 A1 | 11/2005 | Crosby et al. | |
| 2006/0116296 A1 | 6/2006 | Kippie et al. | |
| 2006/0194700 A1 | 8/2006 | Gatlin et al. | |
| 2008/0058229 A1* | 3/2008 | Berkland | C09K 8/516 507/211 |
| 2012/0078021 A1* | 3/2012 | Durham | C07C 7/20 585/4 |
| 2014/0091262 A1* | 4/2014 | Webber | C09K 8/54 252/391 |
| 2015/0011453 A1* | 1/2015 | Bennett | C11D 3/2006 510/402 |
| 2015/0118105 A1* | 4/2015 | Liu | C23F 11/124 422/17 |

OTHER PUBLICATIONS

Int'l Search Report and Written Opinion in PCT/US2016/013379, dtd Apr. 28, 2016.

* cited by examiner

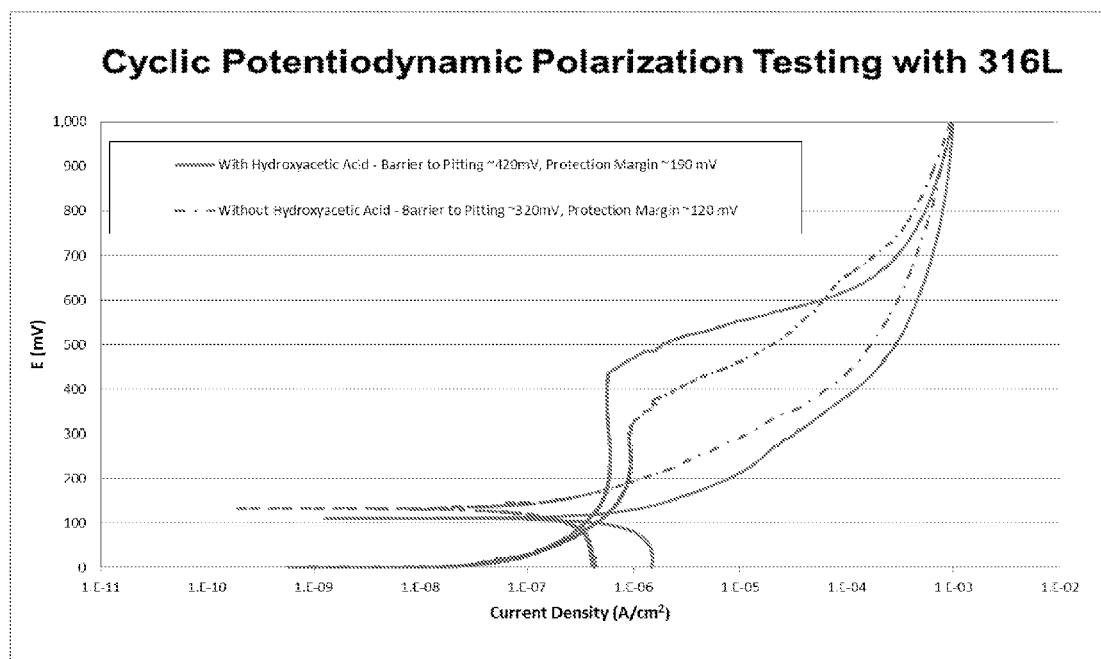

USE OF HYDROXYACID TO REDUCE THE LOCALIZED CORROSION POTENTIAL OF LOW DOSE HYDRATE INHIBITORS

TECHNICAL FIELD

The invention relates to methods and compositions for inhibiting corrosion of metals, and, in one aspect, more particularly relates to methods and compositions for inhibiting localized corrosion of stainless and duplex steels, and still more particularly relates to low dose hydrate inhibitor (LDHI) hydrate inhibiting formulations that have improved inhibition of localized corrosion of stainless and duplex steels.

TECHNICAL BACKGROUND

It is well known that certain stainless and duplex steel alloys experience localized corrosion and will corrode in aqueous environments. The corrosion is in larger part from the presence of an inorganic halide ion, particularly an inorganic chloride ion, and including, but not necessarily limited to, fluoride, chloride, bromide and iodide. While the rate at which corrosion will occur depends on a number of factors, such as the alloy itself, the hydrogen concentration of the solution often measured as the negative logarithm of the hydrogen ion activity known as pH, the temperature of the environment, the length of contact, etc., some sort of corrosion invariably occurs. Localized corrosion is especially severe and can cause failure of the equipment. Alloy technology has provided materials to withstand the incidental contact of steel with many different solutions, but the corrosion problem is particularly aggravated when there is no choice but to contact steel with halide-containing material or fluids, as in the case of chemical processing where substances containing halides are employed. In some instances attention has turned toward providing corrosion inhibitors in the medium itself to prevent corrosion of the steel surfaces that it must come into contact with, yet still deliver the acid to its ultimate destination.

Specific environments in which an improved corrosion inhibitor would be appreciated include industrial cleaning and hydrocarbon recovery operations. With respect to oil and gas production, it is well known that during the production life of an oil or gas well, the production zone within the well may be chemically treated or otherwise stimulated to enhance the economical production lifetime of the well.

A large amount of production and workover conduits comprise various steel alloys. These steels were utilized either temporarily or permanently in the well, and treatment and/or stimulation fluids were introduced through them into the well. Sometimes primarily in the drilling and completion of many subterranean wells through formations which contain high concentrations of corrosive fluids such as hydrogen sulfide, carbon dioxide, brine, and combinations of these constituents, the production and workover conduits for use in the wells are now made of high alloy steels. The high alloy steels include, but are not necessarily limited to, chrome steels, duplex steels, stainless steels, martensitic alloy steels, ferritic alloy steels, austenitic stainless steels, precipitation-hardened stainless steels, high nickel content steels, and the like. Often, treatment chemicals are introduced into wells and pipelines in umbilicals that are made of high alloy steels. The high alloy steels include, but are not necessarily limited to, chrome steels, duplex steels, stainless steels, martensitic alloy steels, ferritic alloy steels, austenitic stainless steels, precipitation-hardened stainless steels, high nickel content steels, and the like.

In hydrocarbon recovery production efforts from offshore and subsea platforms, umbilicals and transfer lines are used for subsea chemical injection systems. One concern in these systems is the undesirable formation of hydrates.

Gas hydrate inhibitors may sometimes contain acids which may cause localized corrosion when they come into contact with various steel alloys. A number of hydrocarbons, especially lower-boiling light hydrocarbons, in subterranean formation fluids or natural gas are known to form hydrates in conjunction with the water present in the system under a variety of conditions—particularly at the combination of lower temperature and higher pressure. The hydrates usually exist in solid forms that are essentially insoluble in the fluid itself. As a result, any solids in a formation or natural gas fluid are at least a nuisance for production, handling and transport of these fluids. It is further not uncommon for hydrate solids (or crystals) to cause plugging and/or blockage of pipelines or transfer lines or other conduits, valves and/or safety devices and/or other equipment, resulting in shutdown, loss of production and risk of explosion or unintended release of hydrocarbons into the environment either on-land or off-shore. Accordingly, hydrocarbon hydrates—particularly preventing or inhibiting their occurrence and growth—have been of substantial interest as well as concern to many industries, particularly the petroleum and natural gas industries.

Hydrocarbon hydrates are clathrates, and are also referred to as inclusion compounds. Clathrates are cage structures formed between a host molecule and a guest molecule. A hydrocarbon hydrate generally is composed of crystals formed by water host molecules surrounding the hydrocarbon guest molecules. The smaller or lower-boiling hydrocarbon molecules, particularly $C_1$ (methane) to $C_4$ hydrocarbons and their mixtures, are more problematic because it is believed that their hydrate or clathrate crystals are easier to form. For instance, it is possible for ethane to form hydrates at as high as 4° C. at a pressure of about 1 MPa. If the pressure is about 3 MPa, ethane hydrates can form at as high a temperature as 14° C. Even certain non-hydrocarbons such as carbon dioxide, nitrogen and hydrogen sulfide are known to form hydrates under certain conditions.

There are two broad techniques to overcome or control the hydrocarbon hydrate problems, namely thermodynamic and kinetic. For the thermodynamic approach, there are a number of reported or attempted methods, including water removal, increasing temperature, decreasing pressure, addition of "antifreeze" to the fluid and/or a combination of these. One type of "antifreeze" is methanol. The kinetic approach generally attempts (a) to prevent the smaller hydrocarbon hydrate crystals from agglomerating into larger ones (known in the industry as an anti-agglomerate and abbreviated AA) and/or (b) to inhibit and/or retard initial hydrocarbon hydrate crystal nucleation; and/or crystal growth (known in the industry as a kinetic hydrate inhibitor and abbreviated KHI). Thermodynamic and kinetic hydrate control methods may be used in conjunction.

Quaternary amine chemistry has been proven to be effective for many applications, including, but not necessarily limited to disinfectants, surfactants, fabric softeners, anti-static agents, corrosion inhibitors for carbon dioxide and hydrogen sulfide corrosion of mild steel, as AA for hydrate control, and the like. However, water quality and fluids separation issues upon the application of quaternary amines are industrial-wide technical challenges, therefore thwarting their broad field implementation to replace conventional thermodynamic hydrate inhibitor (THI) methods. Derivatives from quaternary amine technology that itself possesses potentially severe corrosive tendency, such as betaine, also present similar challenges, irrespective of higher raw material cost (RMC) and complex synthesis routes.

Various corrosion inhibitors are known, to which are added other components, such as intensifiers, surfactants, oil wetting components, and the like. U.S. Pat. No. 2,758,970 describes derivatives of rosin amines, which are represented by the formula:

where R is a radical selected from the group consisting of abietyl, hydroabietyl, and dehydroabietyl, Y is the group $CH_2R_1$, X is a radical selected from the group consisting of hydrogen and $CH_2R_1$, and $R_1$ represents alpha ketonyl groups. These rosin amines are noted as useful in reducing the rate of corrosion of metals such as magnesium, aluminum and zinc when they are exposed to the action of a corrosive material such as hydrochloric acid.

Further, U.S. Pat. No. 3,077,454 describes compositions for inhibiting corrosion made by combining certain active hydrogen containing compounds with organic ketones having at least one hydrogen atom on the carbon atom alpha to the carbonyl group and an aldehyde selected from the group consisting of aliphatic aldehydes containing from 1 to 16 carbons, and aromatic aldehydes of the benzene series, having no functional groups other than aldehyde groups, and a fatty acid.

Additionally, Mannich base and thiourea inhibitor compositions and methods of inhibiting the acid attack by aqueous hydrofluoric acid on ferrous metal surfaces, and in particular highly reactive ferrous metal surfaces, are described in U.S. Pat. Nos. 3,992,313 and 4,104,303.

It is also known in the corrosion inhibition art to provide various corrosion inhibition aids (sometimes called corrosion inhibitor intensifiers or simply intensifiers) which are used together with the above and other known corrosion inhibitors. For instance, U.S. Pat. No. 4,871,024 to Cizek (Baker Hughes Incorporated) describes copper metal salt intensifiers and U.S. Pat. No. 4,997,040 to Cizek (Baker Hughes Incorporated) relates to certain acid soluble mercury metal salt intensifiers.

U.S. Pat. No. 3,773,465 concerns an inhibited treating acid for use in contact with ferrous surfaces at temperatures of from about 150° F. to about 450° F. (about 66 to about 232° C.) which contains cuprous iodide (CuI; copper (I) iodide) in a concentration of from about 25 to about 25,000 ppm by weight of the acid. The patent notes that it was discovered that the cuprous iodide produced in situ by reactants which also form free iodine will operate in the inventive manner therein, but show a smaller degree of improvement as compared with combining preformed cuprous iodide with an acid. Thus, the patent teaches that the most preferred reactants for producing cuprous iodide in situ are those which do not produce free iodine.

It would be advantageous if corrosion inhibitor compositions were discovered that would be an improvement over the presently known systems containing inorganic halides. For example, it would be desirable if a non-methanolic solution which contained an inorganic halide also contained a corrosion inhibitor that would reduce corrosion, particularly localized corrosion of the duplex steel that it contacted. There also remains a need for new corrosion inhibitor compositions and methods of use therefore which would work in other acid environments for a wide variety of metals, particularly iron alloys such as steels.

SUMMARY

There is provided, in one non-limiting embodiment, a method to mitigate corrosion in a metal conduit containing a fluid that contains a hydrate inhibitor formulation which in turn includes a hydrate inhibitor, and having an absence of methanol, the method comprising including in or adding into the hydrate inhibitor formulation an effective amount of at least one hydroxyacid or equivalent thereof selected from the group consisting of hydroxyacids having 2 to 20 carbon atoms and at least one hydroxyl group, alkali metal salts of these hydroxyacids, amine salts of these hydroxyacids, and combinations thereof, to mitigate corrosion of the metal conduit.

Further in another non-restrictive version, there is provided a method for mitigating corrosion in a metal conduit containing a fluid that contains a hydrate inhibitor formulation which in turn includes a hydrate inhibitor, and having an absence of methanol, where the method comprises including in or adding to the hydrate inhibitor formulation from about 0.01 wt % to about 10 wt % of at least one hydroxyacid or equivalent thereof, where the hydroxyacid or equivalent includes, but is not necessarily limited to, hydroxyacetic acid, lactic acid, malic acid, tartaric acid, citric acid, salicylic acid, 4-hydroxybenzoic acid, gallic acid, gluconic acid, alkali metal salts of these hydroxyacids, amine salts of these hydroxyacids, and mixtures thereof.

There is additionally provided, in another non-limiting embodiment, a method to mitigate corrosion in a metal conduit containing a fluid comprising a hydrate inhibitor formulation which in turn includes a low dose hydrate inhibitor, at least one inorganic halide ion, and having an absence of methanol, where the method comprises including in or adding to the hydrate inhibitor formulation an effective amount of at least one hydroxyacid or equivalent thereof including, but not necessarily limited to, hydroxyacids having 2 to 20 carbon atoms and at least one hydroxyl group, alkali metal salts of these hydroxyacids, amine salts of these hydroxyacids, and combinations thereof, to mitigate corrosion of the metal conduit, and where the hydrate inhibitor formulation comprises a solvent selected from the group consisting of aromatic solvents, alcohols having 2 to 10 carbon atoms, diols or triols containing 2 to 10 carbon atoms, ketones having 3 to 12 carbon atoms, and mixtures of these solvents.

BRIEF DESCRIPTION OF THE DRAWINGS

FIG. 1 is a graph of cyclic potentiodynamic polarization testing of a fluid without hydroxyacetic acid and with hydroxyacetic acid demonstrating an increased protection margin for the fluid containing hydroxyacetic acid.

DETAILED DESCRIPTION

A new LDHI chemistry was developed. The intent was to reduce the potential for localized corrosion while maintaining low product viscosity by utilizing a methanol solvent package. Localized corrosion potential, although reduced, was not sufficient to allow confident use of the product in subsea chemical injection systems, such as umbilicals and transfer lines. Different solvent packages provided no noticeable reduction for potential localized corrosion. Consequently, a series of additives were studied and one (hydroxyacetic acid), was discovered to be compatible with the new LDHI chemistry and the desired methanol solvent package, and was identified as providing the required reduction in localized corrosion potential with duplex steels. The successful additive allows the LDHI chemistry to maintain the low viscosity required for treating long subsea tie-backs and provide the performance required for hydrate inhibition, all without compromising the integrity of the duplex steels commonly found in topsides and subsea chemical injection systems.

It was subsequently surprisingly discovered that methanol was not required in the new LDHI chemistry. Instead, other solvents may be used, including, but not necessarily limited to, aromatic solvents including, but not necessarily limited to, toluene, xylene and aromatic naphtha; alcohols including, but not necessarily limited to, those having 2 to 10 carbon atoms such as ethanol, 1-propanol, 2-propanol, 1-butanol, 2-butanol, isobutanol and 2-butoxyethanol; ketones including, but not necessarily limited to, those having 3 to 12 carbon atoms such as methyl isobutyl ketone and diisobutyl ketone; diols or triols including, but not necessarily limited to, those containing 2 to 10 carbon atoms such as ethylene glycol, propylene glycol or glycerin, or mixtures and combinations of these solvents.

In many prior formulations an organic acid is used as one component out of three or more components in the corrosion inhibitor or chemical cleaning solutions. It was additionally surprisingly discovered that improved inhibition of localized corrosion could not be achieved in a methanol-containing and halide-containing solution by using an organic hydroxyacid in combination with a number of other corrosion inhibitors. It was discovered that, in one non-limiting embodiment, using the organic hydroxyacid (having at least one hydroxyl group) alone (that is, not as part of a multi-component system) can reduce the localized corrosion susceptibility of stainless and duplex steel in non-methanol-containing and inorganic halide ion-containing solutions.

Material compatibility with storage tanks, injection tubing and umbilical tubes for deep sea applications is a mandatory requirement for chemical products. Many proposed products fail at the last step of commercialization because of material compatibility issues, for instance, they are found to cause localized corrosion, particularly pitting corrosion of stainless and duplex steel. A chemical solution to overcome this pitting problem in non-methanol-containing and inorganic halide-containing solutions was discovered, as described herein.

Many solutions have methanol present as a solvent for lower viscosity and low temperature stability. For instance, the compositions and methods described in U.S. Pat. No. 6,596,911 to John L. Przybylinski and Gordon T. Rivers (Baker Hughes Incorporated) use methanol as a solvent; incorporated by reference herein in its entirety.

Another common approach to address the pitting corrosion problem is to use an aromatic solvent instead of methanol and a relatively minimum amount of water. However, the trade-off is that the resulting solution has high viscosity, which will limit its use in deep water applications and potentially cause injection difficulty. In contrast, the non-methanolic solutions and methods of using them as described herein are expected to be injected according to currently accepted procedures while also inhibiting localized corrosion, such as pitting corrosion.

As previously mentioned, the hydrate inhibitor formulations herein have at least three components: water, a hydrate inhibitor, particularly a LDHI, an optional non-methanol solvent, optionally at least one inorganic halide, and at least one organic hydroxyacid having 2 to 20 carbon atoms and at least one hydroxyl group. In one non-restrictive version, these are the only three components. In one non-limiting embodiment, the water proportion ranges from about 0.01 independently to about 12 wt %, in another non-limiting embodiment from about 0.5 independently to about 10 wt %, alternatively from about 2 wt % independently to about 6 wt %. As used herein with respect to ranges, the term "independently" means that any lower threshold may be combined with any upper threshold to form a suitable alternative range.

The optional non-methanol solvent proportion may range from about 5 independently to about 70 wt %, in another non-limiting embodiment from about 10 independently to about 60 wt %, alternatively from about 15 independently to about 50 wt %. The at least one inorganic halide proportion may range from about 0.5 independently to about 80 wt %, in another non-limiting embodiment from about 5 independently to about 70 wt %, and alternatively from about 10 independently to about 60 wt %. The at least one organic hydroxyacid (or amine salt or alkaline metal salt thereof) may be present from about 0.5 independently to about 10 wt %, alternatively from about 0.75 independently to about 3.5 wt %. In the case of dibutylamine glycolate, a proportion of about 0.1 independently to 5 wt %, alternatively 0.5 up about 1.2 wt % in the formulation may be suitable. Alternatively, where the at least one organic hydroxyacid is glycolic acid, about 0.3 wt % to about 0.9 wt % may be a suitable proportion range; alternatively about 0.6 wt % may be a suitable proportion.

The pH of the formulation may range from about 3.5 independently to about 8; in one non-limiting embodiment from about 4.0 independently to about 7.5; in a different non-restrictive version from about 4.6 independently to about 7.0; alternatively from about 4.9 independently to about 6.5.

Suitable inorganic halides include, but are not necessarily limited to, fluoride, chloride, bromide, iodide and combinations thereof. In one non-limiting embodiment the inorganic halide is an inorganic chloride.

In one non-limiting embodiment, the at least one organic hydroxyacid is a hydroxy acid containing 2 to 10 carbon atoms with at least one hydroxyl group and at least one carboxylic acid group. Suitable organic hydroxyacids include, but are not necessarily limited to, 2-hydroxyacetic acid (glycolic acid), 2-hydroxypropanoic acid (lactic acid), 3-hydroxypropanoic acid (hydracrylic acid), 2-hydroxysuccinic acid (malic acid), citric acid, gluconic acid 2,3-dihydroxybutanedioic acid (tartaric acid), 2-hydroxybutyric acid (alpha-hydroxybutyric acid), 2-hydroxybutyric acid (beta-hydroxybutyric acid, 4-hydroxybutyric acid (gamma-hydroxybutyric acid), 2-hydroxybenzoic acid (salicylic acid), 3-hydroxybenzoic acid, 4-hydroxybenzoic acid, 3,4,5-trihydroxybenzoic acid (gallic acid), and combinations thereof. Further and alternatively, the at least one organic hydroxyacid may include, but not necessarily be limited to, ethanolamine salt of glycolic acid, the butyl amine salt of glycolic acid, the dibutylamine salt of glycolic acid, and combinations thereof. In another non-limiting embodiment the at least one organic hydroxyacid has an absence of tartaric acid and/or an absence of malic acid and/or an absence of citric acid.

Additionally, the hydrate inhibitor formulation and/or method of inhibiting corrosion using the hydrate inhibitor formulation described herein may be practiced in the absence of ethanol. Further, the hydrate inhibitor formulation and/or method of inhibiting corrosion using the hydrate inhibitor formulation described herein may be practiced in the absence of a fuel, particularly in the absence of a transportation fuel, and even more particularly in the absence of gasoline and diesel. In another non-limiting embodiment, the hydrate inhibitor formulation has an absence of an amino alkylene phosphonic acid or its derivatives, and/or alternatively, an absence of one or more of the compounds molybdates, azoles, and/or inorganic metal compounds selected from the group consisting of metal salts such as the nitrates, nitrites, silicates, carbonates, i.e. sodium silicates, sodium nitrite, sodium nitrate, sodium carbonate, potassium nitrite, ammonium silicate, etc. and the metal oxides such as zinc oxide, etc.

As previously mentioned, the hydrate inhibitor formulation has improved localized corrosion with respect to stainless and duplex stainless steel as compared with an otherwise identical hydrate inhibitor formulation absent the at least one organic hydroxyacid. In a different non-limiting embodiment, the at least one organic hydroxyacid is the only corrosion inhibitor in the hydrate inhibitor formulation.

While it is expected that methods and compositions using the hydrate inhibitor formulation as described herein will find particular applicability in the inhibition and/or prevention of localized corrosion of stainless steels, it should be further appreciated that the methods and compositions using the hydrate inhibitor formulation as described herein will find particular applicability in the inhibition and/or prevention of corrosion for mild steels, and/or for the inhibition and/or prevention of general corrosion. The corrosion-inhibiting additives of carboxylic acids having from 2 to 20 carbon atoms with at least one hydroxyl group are expected to mitigate the pitting corrosion of single phase stainless steels such as 316 and 304, as well as mitigating the pitting corrosion of duplex steels such as 19D and 2205. It is also expected to limit the general corrosion of carbon steels such as 1010.

I. SEKINE, et al., "Analysis for Corrosion Behavior of Mild Steels in Various Hydroxy Acid Solutions by New Methods of Surface Analysis and Electrochemical Measurements," *J. Electrochemical Soc.*, Vol 137, No. 10, October 1990, pp. 3029-3033 indicated that corrosion rates of mild steel with aqueous glycolic acid solutions is lower than other hydroxyacid solutions. However, corrosion inhibition is not mentioned. It may be further discovered that the hydrate inhibitor formulations described herein may also find utility in applications for the prevention or inhibition of scale formation.

The dosage or effective amount of hydrate inhibitor formulation corrosion inhibitor may vary greatly depending on the type of chemistry used, and other factors including, but not necessarily limited to the acid used, the acid strength, tubular metallurgy (the nature of the steel contacted), the temperature of the well system, expected acid exposure time, the nature or composition of the mixture of water and hydrate-forming guest molecules, etc. However, in one non-limiting embodiment, the amount of corrosion inhibitor in the total aqueous acidic composition (including water, acid and corrosion inhibitor) may range from about 0.01 independently to about 10 wt %, in another non-limiting embodiment from about 0.20 independently to about 2.0 volume %.

Alternatively, additional corrosion inhibitors which may be used with the formulations herein include, but are not necessarily limited to Mannich reaction products, quaternary amine compounds, acetylenic alcohols and combinations thereof. In one non-limiting embodiment, useful corrosion inhibitor bases are the Mannich reaction products, which may include, but are not necessarily limited to, the materials of U.S. Pat. Nos. 3,077,454; 5,366,643; and 5,591,381. The products of U.S. Pat. No. 3,077,454 may be made with approximately a 50% yield, and they require the presence of a fatty acid, such as a tall oil fatty acid, in one non-limiting embodiment. The texts of these patents are incorporated by reference herein in their entireties. More specifically, the Mannich reaction product may be the product of reaction of (i) one mole of an ammonia derivative having at least one hydrogen attached to nitrogen and having no groups reactive under the conditions of reaction other than hydrogen, (ii) from 1.5 to 10 moles of a carbonyl compound having at least one hydrogen atom on the carbon atom adjacent to the carbonyl group, (iii) from 2 to 10 moles of an aldehyde different from the carbonyl compound selected from the group consisting of aliphatic aldehydes having from 1 to 16 carbon atoms and aromatic aldehydes of the benzene series and having no functional groups other than aldehyde groups, and (iv) from 0.6 to 24 parts by weight based on (1), (2), and (3) of an organic acid having from 1 to 20 carbon atoms, at a temperature of from about 150° F. (66° C.) to about 250° F. (121° C.) for from about 1 to 16 hours.

One suitable non-limiting Mannich reaction based acid corrosion inhibitor is comprised of the condensation reaction product of 1,3-dibutyl thiourea and acetophenone. Baker Hughes CI 200 inhibitor is a corrosion inhibitor of this type. They contain acetylenic alcohols as well as oxyalkylated alcohol surfactant dispersants, in a co-solvent system containing methanol and fatty acid derivatives.

Baker Hughes CI 300 inhibitor is a suitable quinoline quaternary amine-based acid corrosion inhibitor containing cinnamic aldehyde, as well as oxyalkylated linear alcohol dispersants in a mixed solvent system containing primary alcohols and aromatic naphtha.

Suitable quaternary amine compounds may include, but are not necessarily limited to, the nitrogen-substituted heterocycles of 6 to 10 members quaternized with alkyl halides, also commonly referred to as coal tar based quats. These materials are typically quinolines, pyridines and the like quaternized with alkyl and/or aryl halides, where the alkyl or aryl group may range from methyl to benzyl ($C_1$ to $C_6$). Naphthyl quinoline quats are included in this group. Further information may be found with reference to U.S. Pat. No. 2,814,593, incorporated by reference herein in its entirety, which discusses benzyl chloride quats of quinoline.

Other optional ingredients may be used with the corrosion inhibitor herein, and may include, but are not necessarily limited to, any acetylenic compound such as acetylenic alcohols; cinnamaldehyde; nitrogen compounds, such as a quarternary ammonium compounds; solvents such as alcohols or ketones; and aromatic hydrocarbons or mixtures thereof, as are known to those skilled in the art. For example, teachings from acid corrosion inhibitors as made and described in U.S. Pat. Nos. 3,514,410; 3,404,094; 3,107,221; 2,993,863; and 3,382,179; may be utilized herein. All of these patents are hereby incorporated by reference herein in their entirety. In one non-restrictive embodiment, the corrosion inhibitor contains at least one acetylenic alcohol having from 3 to 10 carbon atoms. In another non-limiting embodiment herein however, the corrosion inhibitor excludes and/or has an absence of acetylenic alcohol.

Examples of acetylenic compounds that may be optionally used include propargyl alcohol (2-propyn-1-ol), hexynol, dimethyl hexynol, diethyl hexynediol, dimethyl hexynediol, ethyl octynol, dimethyl octynediol, methyl butynol, methyl pentynol, ethynyl cyclohexynol, 2-ethyl hexynol, phenyl butynol, and ditertiary acetylenic glycol.

Other acetylenic compounds which can be optionally employed include, but are not limited to, butynediol; 1-ethynylcyclohexanol; 3-methyl-1-nonyn-3-ol; 2-methyl-3-butyn-2-ol, also 1-propyn-3-ol, 1-butyn-3-ol, 1-pentyn-3-ol, 1-heptyn-3-ol, 1-octyn-3-ol, 1-nonyn-3-ol, 1-decyn-3-ol, 1-(2,4,6-trimethyl-3-cyclohexenyl)-3-propyne-1-ol, and in general acetylenic compounds having the general formula:

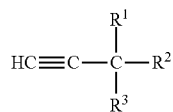

wherein $R^1$ is —H, —OH, or an alkyl radical; $R^2$ is —H, or an alkyl, phenyl, substituted phenyl or hydroxyalkyl radical; and $R^3$ is —H or an alkyl, phenyl, substituted phenyl or hydroxyalkyl radical.

The nitrogen or ammonia compounds that can be optionally employed herein, may include, but are not limited to, those amines having from 1 to 24 carbon atoms in each alkyl moiety as well as the six-membered heterocyclic amines, for example, alkyl pyridines, crude quinolines and mixtures thereof. This includes such amines as ethylamine, diethylamine, triethylamine, propylamine, dipropylamine, tripropylamine, mono-, di- and tripentylamine, mono-, di- and trihexylamine and isomers of these such as isopropylamine, tertiary-butylamine, etc. This also includes alkyl pyridines having from one to five nuclear alkyl substituents per pyridine moiety, such alkyl substituents having from one to 12 carbon atoms, and preferably those having an average of six carbon atoms per pyridine moiety, such as a mixture of high boiling tertiary-nitrogen-heterocyclic compounds, such as HAP (high alkyl pyridines), Reilly 10-20 base and alkyl pyridines H3. Other nitrogen compounds include the crude quinolines having a variety of substituents.

The corrosion inhibitor may also contain a number of other constituents, such as fatty alcohol adducts, nonyl phenol adducts and tallow amine adducts, tall oil adducts, such as surfactants. Oil wetting components, such as heavy aromatic solvents, may also be present. In another non-limiting embodiment, the corrosion inhibitor contains at least one saturated alcohol having from 1 to 5 carbon atoms, and at least one alkyl phenol or alkoxylated alkyl phenol having from 15 to 24 carbon atoms.

Emulsion-preventing surfactants may also be useful to prevent adverse interaction between the hydroxyacid and the reservoir fluids. Suitable commercial surfactants include, but are not necessarily limited to, Baker Hughes NE-100 surfactant. These surfactants may be blends of polyglycols, and may be described as containing 2-ethylhexanol, ethoxyated alcohol, heavy aromatic naphtha, isopropyl alcohol and methanol. They may contain other proprietary surfactants. Many conventional emulsion-breaking surfactants are derived from polyols, esters or resins, with each family having a particular or specialized function such as speed of oil/water separation, oil/water interface quality and oil carryover in the water phase. Baker Hughes also sells AQUET™ 946 and AQUET™ AR30 non-emulsifiers. Typical dosages of emulsion-preventing surfactants may range from about 0.1 to about 0.5% by volume of the aqueous acid composition.

It will be appreciated that the compositions and methods herein will have applicability to other industries besides petroleum recovery, including, but not necessarily limited to, water wells, cleaning industrial machinery, pickling steel in acid, gas hydrate inhibition, other upstream chemical such as scale inhibitors and water clarifiers, pumping acids through pipes, pipelines and other conduits, and other applications where it is desirable to reduce corrosion, such as chemical processes that necessarily require the contact of acids etc. While the specific implementation of the methods and compositions herein is described in the context of the oil patch, they may certainly find uses in conduits, fittings, and other equipment, such as industrial cleaning applications. It will be appreciated that one of ordinary skill in the art of corrosion inhibition will be able to adapt the teachings herein to applications outside the realm of oil and gas recovery, such as the area of chemical processing, with only routine experimentation.

It will also be appreciated that it is not necessary that corrosion be entirely prevented for the methods described herein to be considered successful, although corrosion prevention is a goal. The methods may be considered successful if corrosion is inhibited or reduced as compared with an identical formulation composition which does not have at least one organic hydroxyacid, as described herein.

In the implementation of the methods and corrosion inhibitors herein in the production of fluids from subterranean reservoirs, a fluid may be introduced through a high alloy steel member or conduit positioned within the well or other umbilical or transfer line. The corrosion inhibitor herein is introduced, added, or injected into the fluid. As noted, the fluid may contain an acid. The fluid may be an acidic injection medium and in most cases is expected to include an acid corrosion inhibitor.

An alternative fluid which is contemplated for use in one non-limiting aspect of the methods and compositions herein is one for treatment of a subterranean well for enhancement of production such as an aqueous based fluid; e.g., it will be formed using sea water available at the well location, a brine, tap water or similar fluid. The amount of fluid used for the treatment will vary, of course, from well to well, and will be based upon the particular application at hand, and the amount thereof is not particularly critical to the method.

The compositions and methods may also optionally contain iron control agents to prevent corrosion byproducts from precipitating in the reservoir. The dosage varies with the type of iron control agents used. Suitable iron control agents include, but are not necessarily limited to, citric acid, erythorbic acid and sodium erythorbate, nitrilotriacetic acid (NTA) and salts thereof, ethylene diamine tetraacetic acid (EDTA) and salts thereof, and acetic acid.

The invention will be described further in the following illustrative Examples, which are non-limiting and serve only to further illuminate the compositions and methods described herein.

EXAMPLE 1

The research work leading to the compositions and methods described herein started with previous investigations into the use of hydroxyacetic acid to reduce the localized corrosion potential of organic halide-containing methanolic solutions. Various formulations were tried and it was found that the improvement could not be repeated. Methanol was subsequently removed as a solvent.

FIG. 1 is a graph of cyclic potentiodynamic polarization (CPP) testing of a fluid without hydroxyacetic acid and with hydroxyacetic acid demonstrating an increased protection margin for the fluid containing hydroxyacetic acid; CPP is an electrochemical measure of localized corrosion potential. The cyclic potentiodynamic polarization testing was conducted at room temperature and atmospheric conditions with a constant sparge and mixing of a 98 mole % nitrogen/2 mole % oxygen gas into the fluid. A saturated potassium chloride+silver chloride electrode was used as the reference electrode, a HASTELLOY® rod was used as the counter electrode, and a 316L stainless steel rod was used for or the working electrode. The fluid comprised: 56.05 wt % oxazolidinium quat compound previously described in U.S. Pat. No. 8,575,358 B2 (incorporated herein by reference in its entirety), 3.95 wt % water and 37 wt % toluene. The fluid either had no hydroxyacetic acid (glycolic acid) or had 3 wt % of hydroxyacetic acid substituted for equal wt % toluene. The aqueous glycolic acid was 70 wt % glycolic acid and 30 wt % water. The curve for the fluid without hydroxyacetic acid is the dashed curve; the curve for the fluid with hydroxyacetic acid is the solid curve. The key areas of interest when interpreting a CPP curve are: 1) $E_{ref}$—the open circuit potential or baseline of the curve. 2) $E_{pit}$—as the voltage sweeps during the test, a smooth gradient is observed. If the metal begins to pit, the gradient decreases/current density dramatically increases. This inflection point is called the $E_{pit}$. 3) Repassivation/$E_{prot}$—when the voltage reverses (due to maximum voltage or maximum current density being reached) a hysteresis loop may be observed (where the reverse curve dissects the initial curve). This point of dissection is called the $E_{prot}$. These three areas help determine the pitting susceptibility of the fluid in the presence of 316L stainless steel. $E_{pit}$ minus $E_{ref}$ is defined as the barrier to pitting and $E_{prot}$ minus $E_{ref}$ is defined as the protection margin. It is noted that the test for the fluid that contained hydroxyacetic acid had a larger barrier to pitting (~420 mV versus ~320 mV) and larger protection margin (~190 mV versus ~120 mV) than the fluid without hydroxyacetic acid. This reduction in corrosivity is surprisingly reduced significantly, even though additional water was present.

A larger barrier to pitting and larger protection margin indicates a lower pitting susceptibility. As noted, the organic acid was hydroxyacetic acid (glycolic acid). The low oxygen environment is defined as 2 mole % oxygen.

With respect to the compositions and methods described herein, organic hydroxy acids have been identified as effective to reduce pitting corrosion susceptibility of stainless steel in non-methanolic solutions containing inorganic halides. Suitable ranges of organic acid, pH and additional water content have been identified. The methods and compositions discussed herein may provide solutions for inorganic halide-containing products to overcome their high pitting corrosion tendency. By using the approach described herein, an organic halide-containing non-methanolic solution as described herein may meet customers' requirements concerning material compatibility, with reduced pitting susceptibility. Improvement in pitting corrosion reduction was also achieved for other products tested. It will be appreciated that an optimal condition may need to be identified with every applicable product.

Many modifications may be made in the present invention without departing from the scope thereof that are defined only by the appended claims. For example, certain components per se, or combinations of components thereof other than those specifically set out herein may be found by one of routine skill in the art to be particularly advantageous, e.g. different combinations of corrosion inhibitors with different acids, different hydrate inhibitors, different solvents, different metals, different inorganic halides, different organic hydroxyacids with certain optional solvents and/or optional acids, surfactants and/or dispersants, etc. other than those mentioned or exemplified are expected to be useful.

The words "comprising" and "comprises" as used throughout the claims is interpreted "including but not limited to".

The present invention may suitably comprise, consist or consist essentially of the elements disclosed and may be practiced in the absence of an element not disclosed. For instance, in one non-limiting embodiment, there may be provided a method to mitigate corrosion in a metal conduit containing a fluid comprising a hydrate inhibitor formulation comprising a hydrate inhibitor, and having an absence of methanol, where the method consists essentially of or consists of including in or adding to the hydrate inhibitor formulation an effective amount of at least one hydroxyacid or equivalent thereof selected from the group consisting of hydroxyacids having 2 to 20 carbon atoms and at least one hydroxyl group, alkali metal salts of these hydroxyacids, amine salts of these hydroxyacids, and combinations thereof, to mitigate corrosion of the metal conduit.

There is additionally provided in another non-restrictive version, a method of mitigating corrosion in a metal conduit containing a fluid comprising a hydrate inhibitor formulation comprising a hydrate inhibitor, and having an absence of methanol, where the method consists essentially of or consists of including in or adding to the hydrate inhibitor formulation from about 0.01 wt % to about 10 wt % of at least one hydroxyacid or equivalent thereof, where the hydroxyacid or equivalent is selected from the group consisting of hydroxyacetic acid, lactic acid, malic acid, tartaric acid, citric acid, salicylic acid, 4-hydroxybenzoic acid, gallic acid, gluconic acid, alkali metal salts of these hydroxyacids, amine salts of these hydroxyacids, and mixtures thereof.

Alternatively there may be provided in another non-limiting embodiment a method to mitigate corrosion in a metal conduit containing a fluid comprising a hydrate inhibitor formulation comprising a low dose hydrate inhibitor and at least one inorganic halide ion, and having an absence of methanol, where the method consists essentially of or consists of including in or adding to the hydrate inhibitor formulation an effective amount of at least one hydroxyacid or equivalent thereof selected from the group consisting of hydroxyacids having 2 to 20 carbon atoms and at least one hydroxyl group, alkali metal salts of these hydroxyacids, amine salts of these hydroxyacids, and combinations thereof, to mitigate corrosion of the metal conduit, and where the hydrate inhibitor formulation comprises a solvent selected from the group consisting of aromatic solvents, alcohols having 2 to 10 carbon atoms, diols or triols containing 2 to 10 carbon atoms, ketones having 3 to 12 carbon atoms, and mixtures of these solvents.

What is claimed is:

1. A method to mitigate corrosion in a metal conduit containing a fluid comprising a hydrate inhibitor formulation comprising a hydrate inhibitor and at least one inorganic halide ion, and having an absence of methanol, the method comprising including in the hydrate inhibitor formulation an effective amount of at least one hydroxyacid or equivalent thereof selected from the group consisting of hydroxyacids having 2 to 20 carbon atoms and at least one hydroxyl group, alkali metal salts of these hydroxyacids, amine salts of these hydroxyacids, and combinations thereof, to mitigate corrosion of the metal conduit.

2. The method of claim 1 where the at least one inorganic halide ion is selected from the group consisting of fluoride, chloride, bromide, iodide and combinations thereof.

3. The method of claim 1 where the hydrate inhibitor formulation has an absence of an organic halide.

4. The method of claim 1 where the hydrate inhibitor formulation comprises a solvent selected from the group consisting of aromatic solvents, alcohols having 2 to 10 carbon atoms, diols or triols containing 2 to 10 carbon atoms, ketones having 3 to 12 carbon atoms, and mixtures of these solvents.

5. The method of claim 1 where the hydroxyacid or equivalent is selected from the group consisting of hydroxyacetic acid, lactic acid, malic acid, tartaric acid, citric acid, salicylic acid, 4-hydroxybenzoic acid, gallic acid, gluconic acid, alkali metal salts of these hydroxyacids, amine salts of these hydroxyacids, and mixtures thereof.

6. The method of claim 1 where the effective amount of hydroxyacid in the hydrate inhibitor formulation ranges from about 0.01 wt % to about 10 wt %.

7. The method of claim 1 where the fluid has improved localized corrosion with respect to the metal conduit when it is in contact with the metal conduit as compared with an otherwise identical fluid absent the at least one hydroxyacid.

8. The method of claim 1 where the at least one hydroxyacid or equivalent thereof is the only corrosion inhibitor in the hydrate inhibitor formulation.

9. The method of claim 1 where the metal conduit is selected from the group consisting of an umbilical, a transfer line, a pipeline, injection tubing, and combinations thereof.

10. The method of claim 9 where the metal conduit comprises a metal selected from the group consisting of duplex steels, single phase stainless steels, carbon steels, and combinations thereof.

11. A method to mitigate corrosion in a metal conduit containing a fluid comprising a hydrate inhibitor formulation comprising a low dose hydrate inhibitor and at least one inorganic halide ion, and having an absence of methanol, the method comprising including in the hydrate inhibitor formulation from about 0.01 wt % to about 10 wt % of at least one hydroxyacid or equivalent thereof, where the hydroxyacid or equivalent is selected from the group consisting of hydroxyacetic acid, lactic acid, malic acid, tartaric acid, citric acid, salicylic acid, 4-hydroxybenzoic acid, gallic acid, gluconic acid, alkali metal salts of these hydroxyacids, amine salts of these hydroxyacids, and mixtures thereof.

12. The method of claim 11 where the hydrate inhibitor formulation has an absence of an organic halide.

13. The method of claim 11 where the hydrate inhibitor formulation comprises a solvent selected from the group consisting of aromatic solvents, alcohols having 2 to 10 carbon atoms, diols or triols containing 2 to 10 carbon atoms, ketones having 3 to 12 carbon atoms, and mixtures of these solvents.

14. A method to mitigate corrosion in a metal conduit containing a fluid comprising a hydrate inhibitor formulation comprising a low dose hydrate inhibitor and at least one inorganic halide ion, and having an absence of methanol, the method comprising including in the hydrate inhibitor formulation an effective amount of at least one hydroxyacid or equivalent thereof selected from the group consisting of hydroxyacids having 2 to 20 carbon atoms and at least one hydroxyl group, alkali metal salts of these hydroxyacids, amine salts of these hydroxyacids, and combinations thereof, to mitigate corrosion of the metal conduit, and where the hydrate inhibitor formulation comprises a solvent selected from the group consisting of aromatic solvents, alcohols having 2 to 10 carbon atoms, diols or triols containing 2 to 10 carbon atoms, ketones having 3 to 12 carbon atoms, and mixtures of these solvents.

15. The method of claim 14 where the hydrate inhibitor formulation has an absence of an organic halide.

16. The method of claim 14 where the hydroxyacid or equivalent thereof is selected from the group consisting of hydroxyacetic acid, lactic acid, malic acid, tartaric acid, citric acid, salicylic acid, 4-hydroxybenzoic acid, gallic acid, gluconic acid, alkali metal salts of these hydroxyacids, amine salts of these hydroxyacids, and mixtures thereof.

17. The method of claim 14 where the effective amount of hydroxyacid in the hydrate inhibitor formulation ranges from about 0.01 wt % to about 10 wt %.

* * * * *